US009323900B2

(12) United States Patent
Kuwaoka et al.

(10) Patent No.: US 9,323,900 B2
(45) Date of Patent: Apr. 26, 2016

(54) ANALYSIS SYSTEM, ANALYSIS DEVICE, AND MANAGEMENT DEVICE

(71) Applicant: Sysmex Corporation, Kobe-shi, Hyogo (JP)

(72) Inventors: Shiro Kuwaoka, Kobe (JP); Taisuke Nishida, Kobe (JP); Shunsuke Yao, Kobe (JP)

(73) Assignee: SYSMEX CORPORATION, Kobe-shi, Hyogo (JP)

( * ) Notice: Subject to any disclaimer, the term of this patent is extended or adjusted under 35 U.S.C. 154(b) by 0 days.

(21) Appl. No.: 14/496,776

(22) Filed: Sep. 25, 2014

(65) Prior Publication Data

US 2015/0012227 A1    Jan. 8, 2015

Related U.S. Application Data

(63) Continuation of application No. PCT/JP2013/001970, filed on Mar. 22, 2013.

(30) Foreign Application Priority Data

Mar. 29, 2012  (JP) .................................. 2012-077486

(51) Int. Cl.
*G01N 33/50* (2006.01)
*G06F 19/00* (2011.01)
*G01N 35/00* (2006.01)
*G01N 31/22* (2006.01)

(52) U.S. Cl.
CPC ................ *G06F 19/70* (2013.01); *G01N 31/22* (2013.01); *G01N 33/50* (2013.01); *G01N 35/00871* (2013.01); *G01N 2035/00673* (2013.01); *G01N 2035/00851* (2013.01)

(58) Field of Classification Search
CPC ...................................................... G01N 33/50
USPC ........................................................... 702/22
See application file for complete search history.

(56) References Cited

U.S. PATENT DOCUMENTS

2008/0240991 A1* 10/2008 Wakamiya ....... G01N 35/00663
422/68.1
2013/0266484 A1* 10/2013 Kamihara ........ G01N 35/00613
422/82.09

* cited by examiner

*Primary Examiner* — Bryan Bui
(74) *Attorney, Agent, or Firm* — Brinks Gilson & Lione

(57) ABSTRACT

An analysis system comprising: an analysis device that analyzes a sample using a reagent and that performs the analysis of the sample in accordance with a measurement parameter measured in relation to a reagent to be used; and a management device communicably connected to the analysis device via a network; wherein the analysis device includes a first control unit that enables execution of processing for accepting a registration of the measurement parameter, and when the measurement parameter is registered, executes processing for transmitting to the management device transmission information including information indicating that the measurement parameter is registered; and the management device includes a second control unit that executes a receiving process of receiving the transmission information transmitted from the analysis device and an output process of outputting information indicating that the measurement parameter is registered in the analysis device based on the received transmission information is disclosed.

19 Claims, 12 Drawing Sheets

FIG. 11

Measurement parameter registration check

- Reagent ID  *** ← 701
- Reagent name *** ← 702
- Measurement item  P-FDP ← 703

705 Reference value

| | | | |
|---|---|---|---|
| 704a → Sample aspiration amount | 14 | 15~18 | [μL] |
| 704b → Diluted solution amount | 110 | 105~126 | [μL] |
| 704c → First reagent amount | 72 | 58~70 | [μL] |
| 704d → Warming time | 30 | 28~32 | [sec] |
| 704e → Second reagent amount | 94 | 88~106 | [μL] |
| 704f → Absorbance changing amount calculation start time | 13 | 11~15 | [sec] |
| 704g → Absorbance changing amount calculation end time | 180 | 170~190 | [sec] |
| 704h → Wavelength | 575 | 575~575 | [nm] |

OK  Cancel

| | | Lower limit value | Upper limit value | |
|---|---|---|---|---|
| | Measurement parameter reference value setting | | | |
| | Reagent ID *** ← 801 | | | |
| | Reagent name *** ← 802 | | | |
| | Measurement item *** ← 803 | | | |
| 804a → | Sample aspiration amount | 15 | 18 | [μL] |
| 804b → | Diluted solution amount | 105 | 126 | [μL] |
| 804c → | First reagent amount | 58 | 70 | [μL] |
| 804d → | Warming time | 28 | 32 | [sec] |
| 804e → | Second reagent amount | 88 | 106 | [μL] |
| 804f → | Absorbance changing amount calculation start time | 11 | 15 | [sec] |
| 804g → | Absorbance changing amount calculation end time | 170 | 190 | [sec] |
| 804h → | Wavelength | 575 | 575 | [nm] |

800

OK | Cancel

ANALYSIS SYSTEM, ANALYSIS DEVICE, AND MANAGEMENT DEVICE

RELATED APPLICATIONS

This application is a continuation of PCT/JP2013/001970 filed on Mar. 22, 2013, which claims priority to the Japanese Application No. 2012-077486 filed on Mar. 29, 2012. The entire contents of these applications are incorporated herein by reference.

TECHNICAL FIELD

The present invention relates to an analysis system, an analysis device, and a management device.

BACKGROUND ART

In analysis devices of biochemical, coagulation, and the like, a reagent for the same measurement item is sold from plural reagent manufacturers. The user selects one of a plurality of reagents, and uses the same for analysis. Each of the reagents has different properties, and thus a measurement parameter such as a dispensing amount, a reaction time, and the like of the reagent needs to be set and registered for each reagent. The analysis device stores the measurement parameter and analyzes a sample in accordance with the stored measurement parameter.

It is desirable that the measurement parameter can be registered (new registration and change) from the standpoint of ensuring the convenience of the user. However, since the measurement parameter is not frequently changed, an appropriate measurement parameter may not be registered due to operation mistakes, lack of knowledge, and the like.

If an appropriate measurement parameter is not registered, the measurement result by the analysis device might be adversely affected.

U.S. Patent Application Publication No. US2010/0054997 discloses an automatic analysis device that includes an operation unit to which an analysis parameter can be input, and in which the analysis parameter can be changed.

In the automatic analysis device described in U.S. Patent Application Publication No. US2010/0054997, in order to prevent the user from accidentally changing the parameter, a password is required when changing the parameter.

In the analysis device described in U.S. Patent Application Publication No. US2010/0054997, the parameter can be suppressed from being accidentally changed by requesting a password, but regardless of such measures, a case in which an erroneous parameter is registered cannot be handled.

SUMMARY OF THE INVENTION

The scope of the present invention is defined solely by the appended claims, and is not affected to any degree by the statements within this summary.

An analysis system according to the first aspect of the present invention relates to an analysis system including an analysis device that analyzes a sample using a reagent and that performs the analysis of the sample in accordance with a measurement parameter measured in relation to a reagent to be used; and a management device communicably connected to the analysis device via a network; wherein the analysis device includes a first control unit that enables execution of processing for accepting a registration of the measurement parameter, and when the measurement parameter is registered, executes processing for transmitting to the management device transmission information including information indicating that the measurement parameter is registered; and the management device includes a second control unit that executes a receiving process of receiving the transmission information transmitted from the analysis device and an output process of outputting information indicating that the measurement parameter is registered in the analysis device based on the received transmission information.

An analysis device according to the second aspect of the present invention relates to an analysis device that analyses a sample using a reagent and that performs the analysis of the sample in accordance with measurement parameter set in relation to a reagent to be used, the analysis device being communicably connected to a management device via a network; the analysis device including a control unit that enables execution of processing for accepting registration of the measurement parameter, and when the measurement parameter is registered, executes processing for transmitting to the management device transmission information including information indicating that the measurement parameter is registered.

A management device according to the fourth aspect of the present invention relates to a management device communicably connected via a network to an analysis device that analyses a sample using a reagent and that performs the analysis of the sample in accordance with measurement parameter set in relation to a reagent to be used, the management device including a control unit that executes a receiving process of receiving transmission information including information indicating that the measurement parameter is registered in the analysis device from the analysis device, and an output process of outputting the information indicating that the measurement parameter is registered in the analysis device based on the received transmission information.

BRIEF DESCRIPTION OF THE DRAWINGS

FIG. 11 is a schematic view showing one example of a measurement parameter registration check screen.

FIG. 12 is a schematic view showing one example of a measurement parameter reference value setting screen.

DETAILED DESCRIPTION OF THE PREFERRED EMBODIMENTS

An embodiment of a sample analysis device according to the present invention will be hereinafter described in detail with reference to the accompanying drawings.

[1. Overall Configuration of Analysis System]

Figure 1:
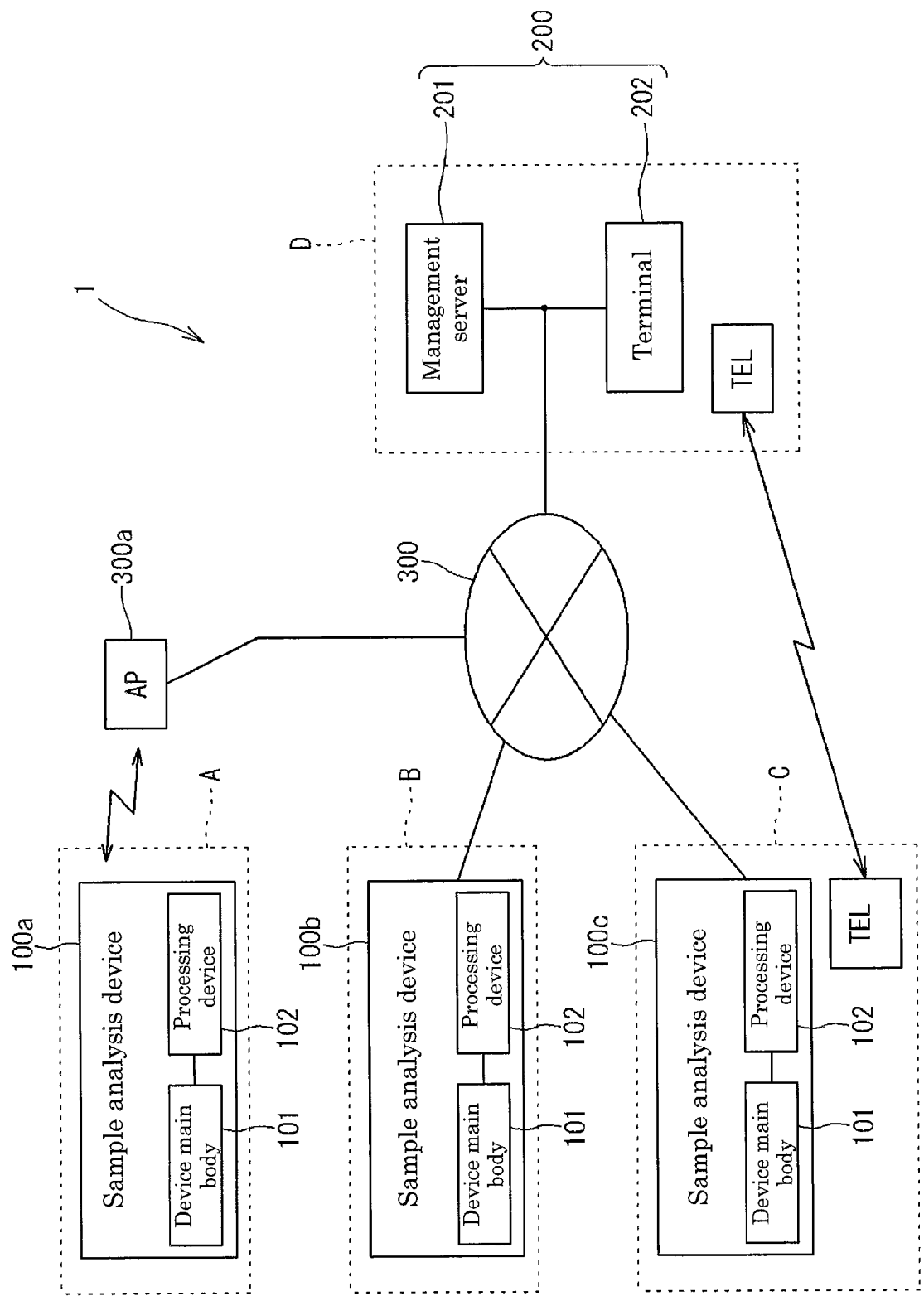
FIG. 1 shows one example of an overall configuration diagram of an analysis system.

FIG. 1 shows an analysis system 1 according to an embodiment. The analysis system 1 includes analysis devices 100a, 100b, 100c, and a management device 200.

The analysis devices 100a, 100b, 100c (hereinafter simply referred to as "analysis device 100" if the plurality of analysis devices does not need to be distinguished) are respectively installed in inspection facilities A, B, C and are connectable to a network 300 such as the Internet.

The management device 200 includes a management server 201 and a terminal device 202, and is installed in a customer support center D. The management server 201 and 202 are connected by the LAN, and are respectively connectable to the network 300 such as the Internet, and the like.

The customer support center D is a facility for a vendor who performs the maintenance of the analysis device 100, and is provided to collect various types of information from the analysis device 100 and perform management with respect to the analysis device 100.

The analysis device 100 is a device for optically measuring and analyzing the amount of specific substance, the degree of activity, and the like associated with coagulation and fibrinolytic function of blood, for example. In the analysis device 100, for example, blood plasma is used, for the sample.

The analysis device 100 performs optical measurement of a sample using coagulation time method, synthetic substrate method, and immune nephelometry. The coagulation time method used in the present embodiment is a measurement method for detecting the process in which the sample coagulates as change in transmissive light. The measurement items of the coagulation time method include PT (prothrombin time), APTT (activity portion thromboplastin time), Fbg (fibrinogen amount), and the like. The measurement items of the synthesis substrate method include ATIII, and the like. The measurement items of the immune nephelometry include D dimer, FDP, and the like.

Figure 2:
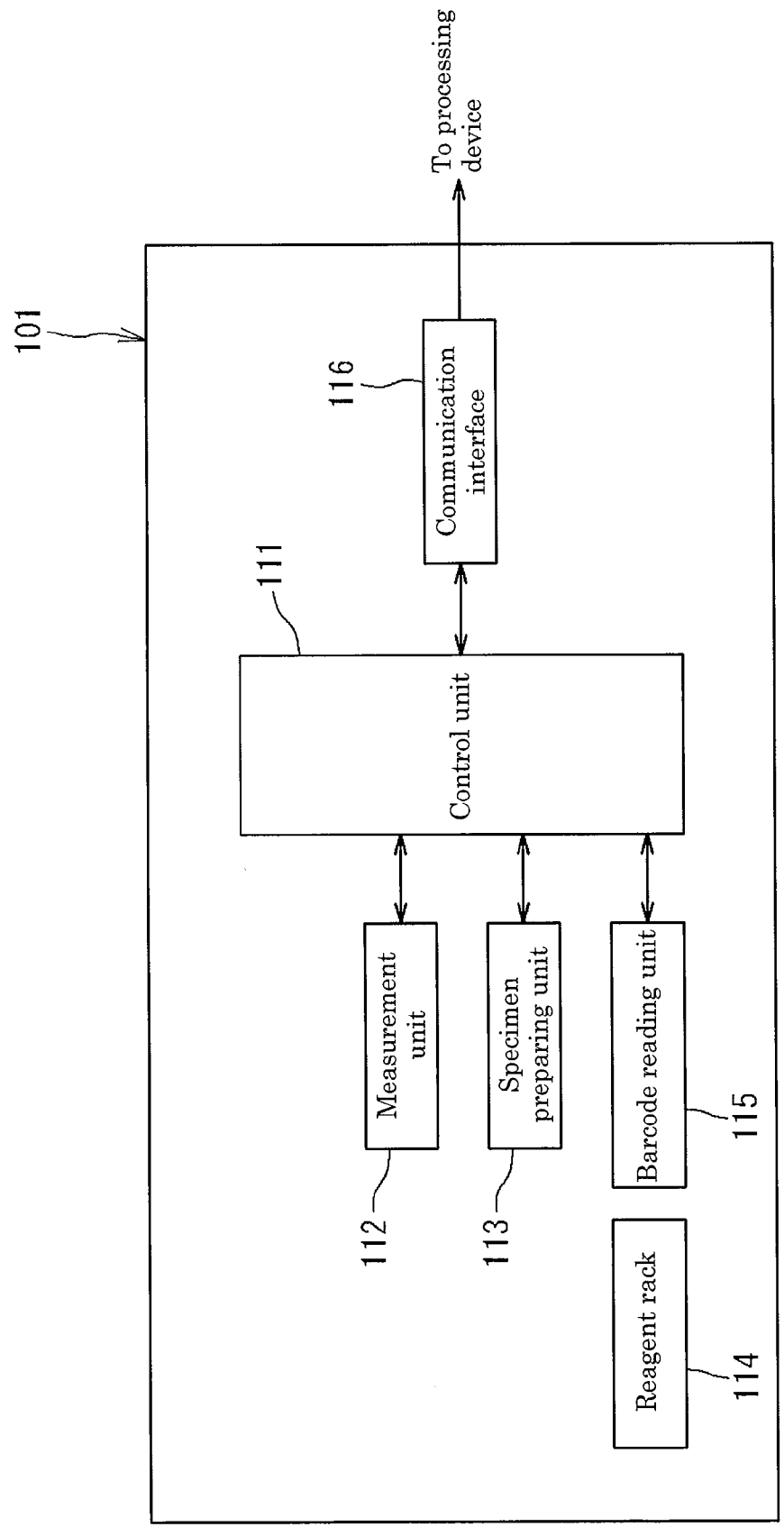
FIG. 2 shows one example of a configuration diagram of a device main body of an analysis device.
Figure 3:
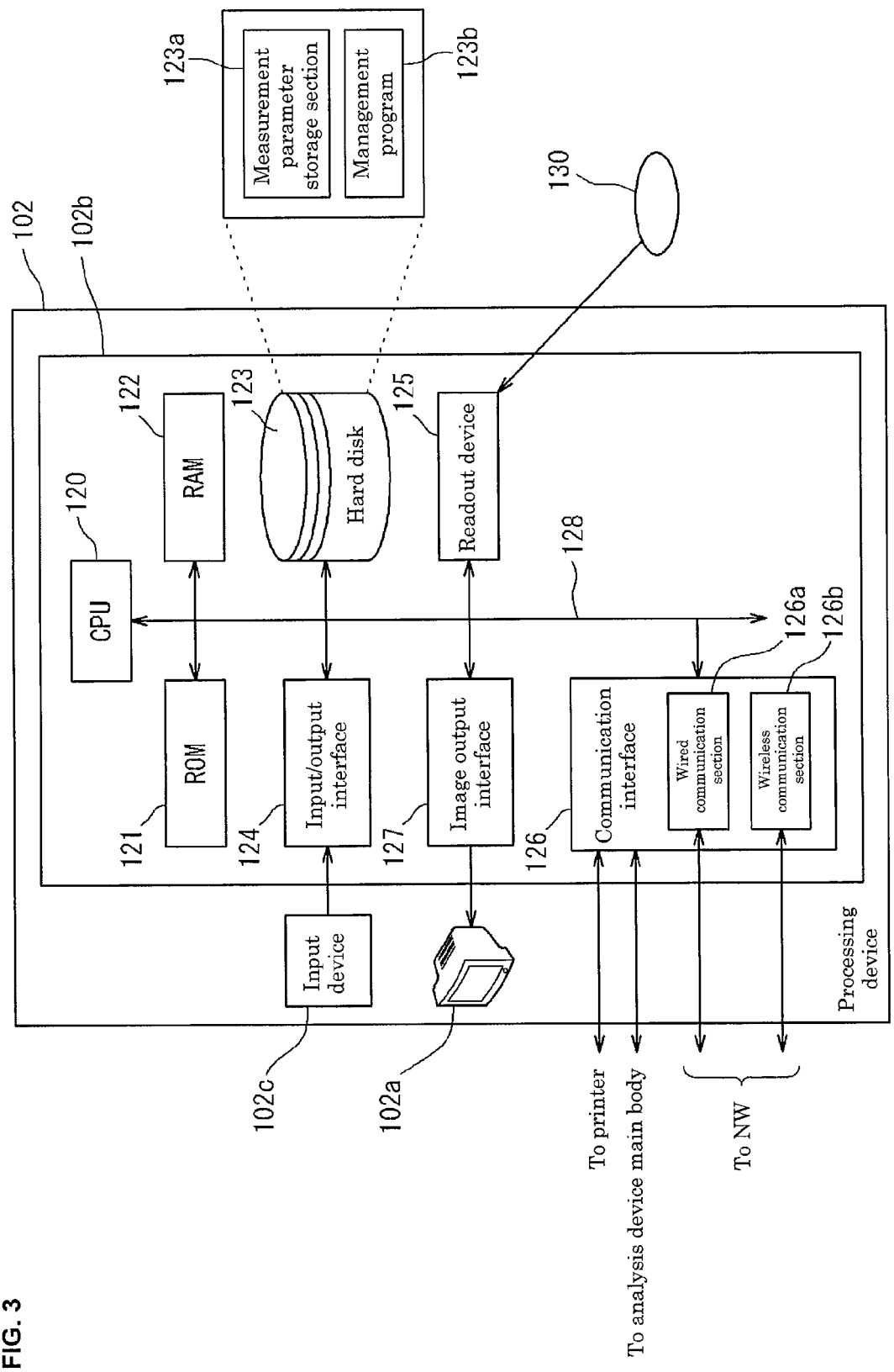
FIG. 3 shows one example of a configuration diagram of a processing device of the analysis device.

As shown in FIGS. 1 to 3, the analysis device 100 includes a device main body 101 and a processing device 102. The device main body 101 and the processing device 102 are communicably connected.

The device main body 101 mainly performs the measurement of the sample. The processing device 102 performs processes such as the analysis process of the measurement result obtained by the device main body 101, the communication with the management device 200 (management server 201), and the like.

As shown in FIG. 2, the device main body 101 includes a control unit 111, a measurement unit 112, a specimen adjusting unit 113, a reagent rack 114, a barcode reading unit 115, a communication interface 116, and the like.

The control unit 111 controls each unit in the device main body 101, and performs the control for reagent preparation, measurement, and the like. The control unit 111 also performs the process of communication carried out with the processing device 102 through the communication interface 116.

The measurement unit 112 performs the measurement (optical measurement) of the specimen prepared from the sample, and outputs the measurement result. The measurement result is transmitted to the processing device 102 by the control unit 111.

A specimen preparing unit 113 is a mechanism for preparing the specimen for measurement from the sample to be analyzed. The specimen preparing unit 113 mixes the reagent in a reagent container set in the reagent rack 114 to the sample (blood plasma) to obtain a measurement specimen.

The barcode reading unit 115 reads a barcode given to the reagent container, and the like set in the reagent rack 114. The barcode of the reagent container includes information for specifying the detailed information (information such as reagent name, type of reagent container, lot number, expiration date of reagent, etc.) of the reagent contained in the reagent container.

The detailed information of the reagent is transmitted to the processing device 102 by the control unit 111, and managed in the processing device 102.

As shown in FIG. 3, the processing device 102 is a computer mainly configured from a display 102a, a main body 102b, and an input device 102c.

The main body 102b is mainly configured by a CPU (processing unit) 120, a ROM 121, a RAM 122, a hard disk 123, an input/output interface 124, a readout device 125, a communication interface 126, and an image output interface 127. The CPU 120, the ROM 121, the RAM 122, the hard disk 123, the input/output interface 124, the readout device 125, the communication interface (transmission unit) 126, and the image output interface 127 are data communicably connected by a bus 128.

The CPU (processing unit) 120 can execute a computer program stored in the ROM 121 as well as a computer program loaded in the RAM 122. When the CPU 120 executes the application program, the function of the processing device 102 is realized and the computer functions as the processing device 102.

The ROM 121 is configured by a mask ROM, a PROM, an EPROM, an EEPROM, and the like, and is recorded with the computer program to be executed by the CPU 120 and the data used for the same.

The RAM 122 is configured by a SRAM, a DRAM, and the like. The RAM 122 is used to read out the computer programs recorded in the ROM 121 and the hard disk 123. The RAM 122 is used as a work region of the CPU 120 when executing the computer programs.

The hard disk 123 is installed with various computer programs (management program 123b) to be executed by the CPU 120 such as the operating system, the application program, and the like, and the data used for the execution of the relevant computer program.

The readout device 125 is configured by a flexible disk drive, a CD-ROM drive, a DVD-ROM drive, and the like, and can read out the computer program or the data recorded in a portable recording medium 130.

The hard disk 123 includes a measurement parameter storage section 123a which is a region that stores a measurement parameter for describing a measurement protocol, the measurement parameter being used for the analysis of the sample, and a region that stores the application program (management program) 123b.

The management program 123b is a program for executing a measurement parameter registration process, a transmission management process, and other necessary processes, to be described later.

In the present embodiment, the measurement parameter storage section 123a is arranged in the processing device 102 of the analysis device 100. However, the measurement parameter storage section 123a may be arranged in the management server 201. In such a case, when registering the measurement protocol, the user first inputs a password, or the like and accesses the management server to perform the registration of the measurement protocol.

The input/output interface 124 is, for example, configured by a serial interface such as an USB, an IEEE 1394, a RS-232C, and the like; a parallel interface such as an SCSI, an IDE, an IEEE 1284, and the like; and an analog interface including a D/A converter, an A/D converter, and the like. An input device 102c including a keyboard and a mouse is connected to the input/output interface 124. The operator can input data to the main body 102b by using the input device 102c.

The communication interface 126 is, for example, the Ethernet (registered trademark) interface. The processing device 102 can transmit and receive data with the device main body 101 using a predetermined communication protocol by the communication interface 126.

The communication interface 126 includes a wired communication section (wired transmission section) 126a and a wireless communication section (wireless transmission section) 126b. The communication interface 126 can carry out the connection to the network 300 through wired connection, or can carry out the connection through wireless connection. The wireless communication section 126b is configured as a wireless communication section for wireless LAN or a wireless communication section for mobile communication such as a cellular phone. The wireless communication section 126b can carry out the wireless communication with an access point (AP) 300a for wireless access, and can carry out communication with the management server 201 via the Internet 300. The access point 300a may be an access point for the wireless LAN, or may be a base station for the cellular phone.

The image output interface 127 is connected to the display 102a configured by an LCD, a CRT, or the like. The CPU 120 outputs a video signal corresponding to the image data to the display 102a via the image output interface 127. The display 102a displays an image (screen) according to the input video signal.

Figure 4:
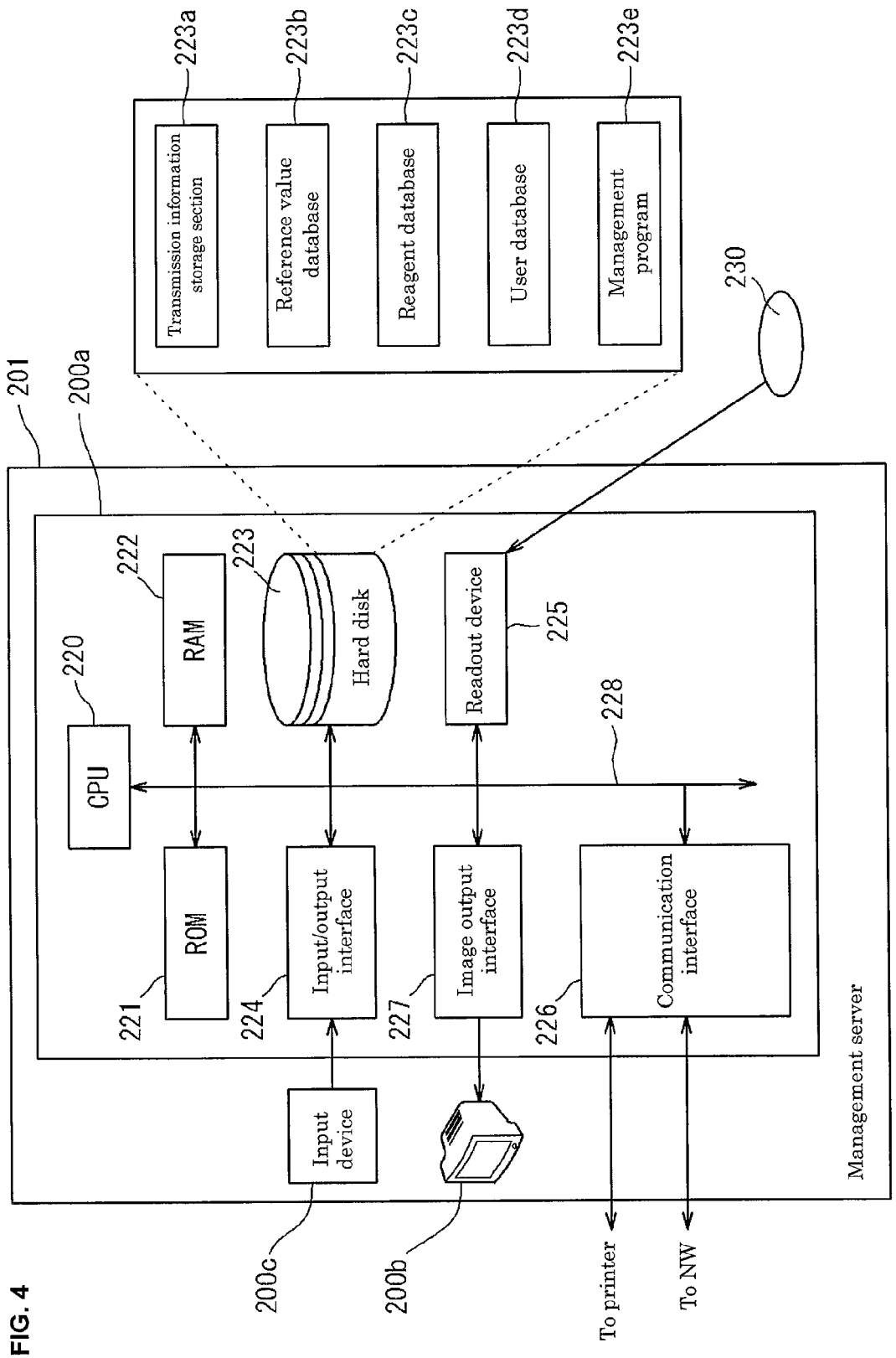
FIG. 4 shows one example of a configuration diagram of a management server.

FIG. 4 shows a block diagram of the management server 201. The management server 201 is a computer mainly configured by a main body 200a, a display 200b, and an input device 200c.

The main body 200a is mainly configured by a CPU 220, a ROM 221, a RAM 222, a hard disk 223, an input/output interface 224, a readout device 225, a communication interface 226, and an image output interface 227. The CPU 220, the ROM 221, the RAM 222, the hard disk 223, the input/output interface 224, the readout device 225, the communication interface 226, and the image output interface 227 are data communicably connected by a bus 228.

The CPU 220 can execute a computer program stored in the ROM 221 as well as a computer program loaded in the RAM 222. When the CPU 220 executes the application program, the function of the management server 201 is realized and the computer functions as the management server 201.

The ROM 221 is configured by a mask ROM, a PROM, an EPROM, an EEPROM, and the like, and is recorded with the computer program to be executed by the CPU 220 and the data used for the same.

The RAM 222 is configured by a SRAM, a DRAM, and the like. The RAM 222 is used to read out the computer programs recorded in the ROM 221 and the hard disk 223. The RAM 222 is used as a work region of the CPU 220 when the computer programs are executed. The hard disk 223 is installed with various computer programs (management program 223e) to be executed by the CPU 220 such as the operating system, the application program, and the like, and the data used for the execution of the relevant computer program.

The readout device 225 is configured by a flexible disk drive, a CD-ROM drive, a DVD-ROM drive, and the like, and can read out the computer program or the data 230a recorded in a portable recording medium 230.

The application program is not only provided by the portable recording medium 230, and may be provided from an external device communicably connected to a computer by an electrical communication line (may be wired or wireless) through the electrical communication line. For example, if the application program is stored in a hard disk of a server computer on the Internet, the management device 200 may access the server computer, download the computer program, and install the computer program in the hard disk 223.

The hard disk 223 is installed with an operating system that provides a graphical user interface environment of Windows (registered trademark) manufactured and sold by US Microsoft Co., for example. In the following description, the application program according to the present embodiment is assumed to operate on the relevant operating system.

Furthermore, the hard disk 223 includes a transmission information storage section 223a which is a region that stores transmission information transmitted from the analysis device, a region that stores a reference value database 223b, a region that stores a reagent database 223c, a region that stores a user database 223d, and a region that stores the application program (management program) 223e.

The reference value database 223b is a database showing a range (reference value) permitted on the management server 201 side as a set value of the measurement parameter. The reference value is a value recommended as the measurement parameter when a reagent manufacturer of the reagent used in the analysis device 100 uses the reagent manufactured by such reagent manufacturer in the analysis device 100. The reagent manufacturer guarantees that appropriate measurement data can be obtained if the measurement parameter is set at such recommended value.

The reagent database 223c is a database in which the reagent having the possibility of being used in the analysis device 100 is registered. The reagent that is not registered in the reagent database 223c is sometimes used in the analysis device 100.

The database 223d is stored with information associated with a user (inspection facility), the information being contact information (telephone number, e-mail address, address of inspection facility, name of contact personnel), and the like, in association with a device ID of the analysis device 100.

The management program 223e is provided to execute the processes necessary to function as the management server such as the server process, and the like, to be described later.

The input/output interface 224 is, for example, configured by a serial interface such as an USB, an IEEE 1394, a RS-232C, and the like; a parallel interface such as an SCSI, an IDE, an IEEE 1284, and the like; and an analog interface including a D/A converter, an A/D converter, and the like. An input device 200c including a keyboard and a mouse is connected to the input/output interface 224. The operator can input data to the main body 200a by using the input device 200c.

The communication interface 226 is, for example, the Ethernet (registered trademark) interface. The management device 201 can transmit and receive data with the analysis device 100 and the terminal device 202 of the support center D connected via the network 300 using a predetermined protocol by the communication interface 226.

The image output interface 227 is connected to the display 200b configured by an LCD, a CRT, or the like. The CPU 220 outputs a video signal corresponding to the image data to the display 200b via the image output interface 227. The display 200b displays an image (screen) according to the input video signal.

[2. Registration Process of Measurement Parameter]

The measurement parameter is stored in the measurement parameter storage section 123a of the processing device 102 as a measurement condition at a time when the measurement of the sample is performed using the reagent such as the dispensing amount, the reaction time, and the like of the reagent. The device main body 101 of the analysis device 100 analyzes (includes measurement) the sample in accordance with the measurement parameter stored in the measurement parameter storage section 123a.

The measurement parameter storage section 123a can store a plurality of measurement parameters corresponding to a plurality of reagents.

Figure 5:
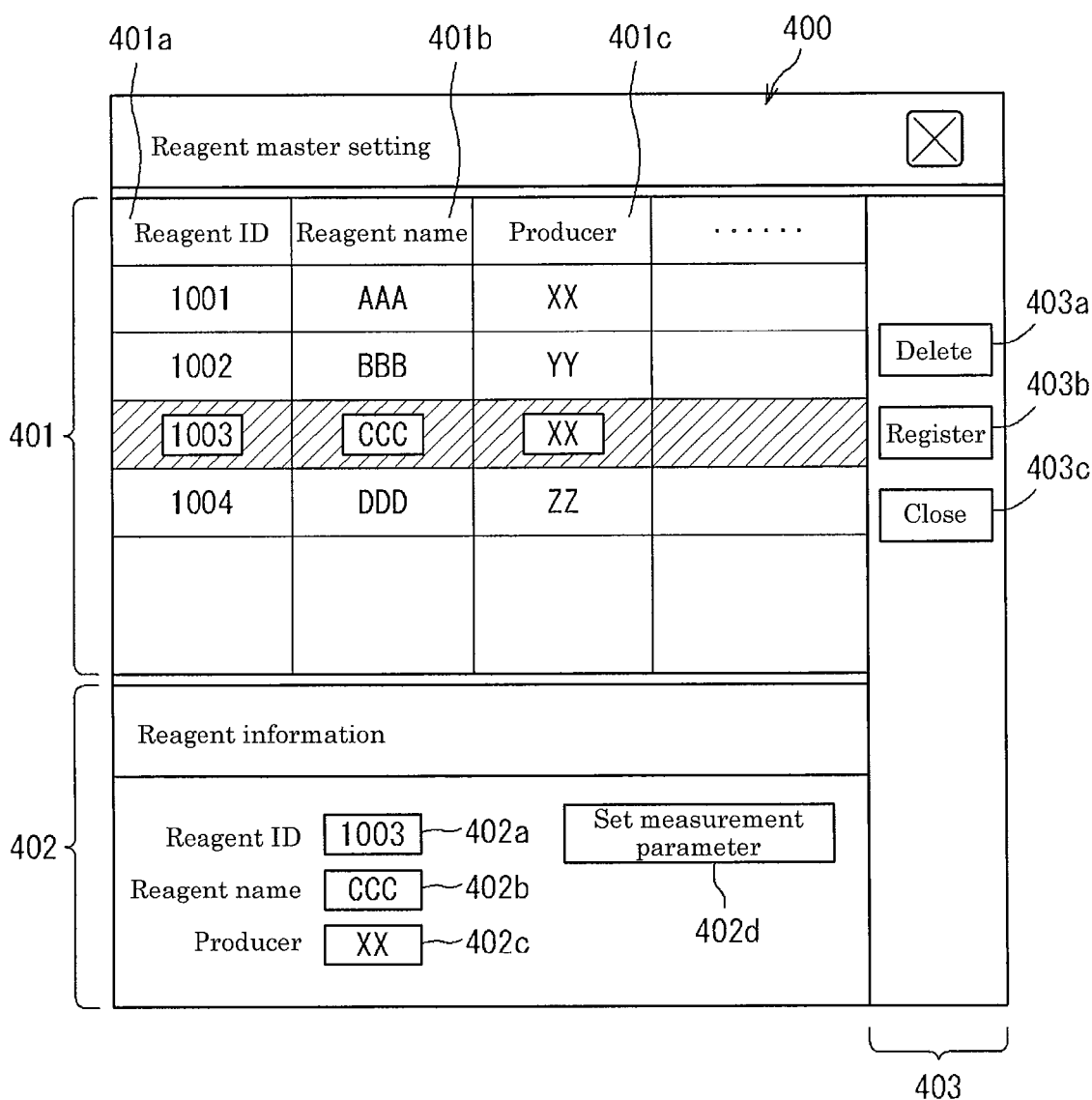
FIG. 5 is a schematic view showing one example of a reagent master setting screen.
Figure 6:
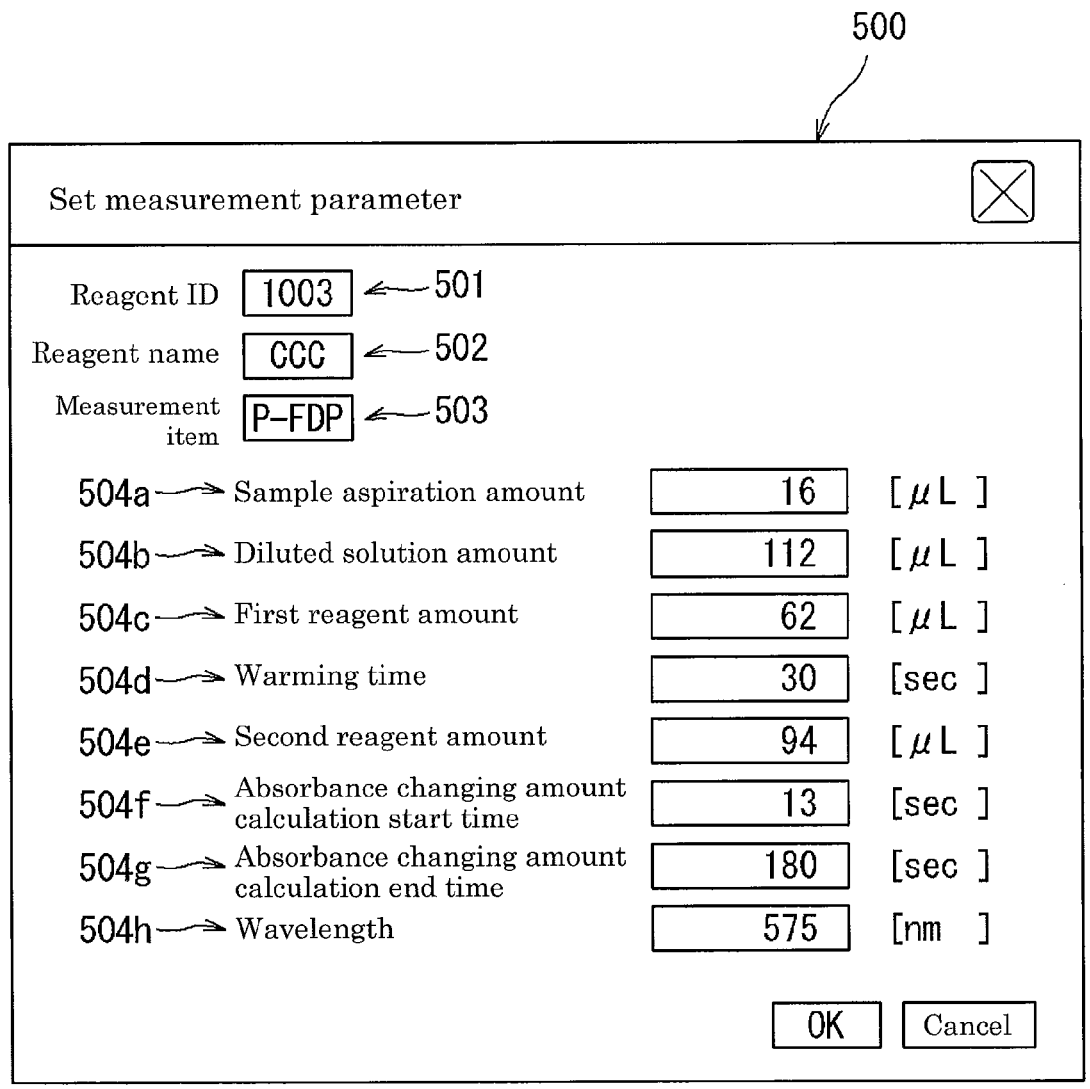
FIG. 6 is a schematic view showing one example of a measurement parameter setting screen.

FIG. 5 and FIG. 6 show screens 400, 500 for the registration (update, add, delete) process of the measurement parameter.

The registered content of the measurement parameter set for every reagent can be changed in accordance with various situations.

For example, even if the reagent is used for the same measurement item, the properties of the reagent differ if the actual producer (manufacturer of the reagent) of the reagent is different. Therefore, when changing the reagent to a reagent of a different manufacturer, a new measurement parameter for the relevant reagent needs to be additionally set.

Furthermore, even if the same reagent is continuously used, the measurement condition may be changed as necessary. In this case, the already set measurement parameter needs to be updated.

Furthermore, the measurement parameter for the reagent, which use is stopped, does not need to be remained set, and may be deleted.

According to the situation described above, the processing device 102 (processing unit 120) of the analysis device 100 can display a reagent master setting screen for changing the measurement parameter shown in FIG. 5 on the display 102a.

The reagent master setting screen includes a reagent list display section 401, a reagent information display section 402, and an operation display section 403.

The reagent list display section 401 displays a list showing a list of reagents registered in the processing device 102. The reagent list display section 401 has fields such as a "reagent ID" 401a, a "reagent name" 401b, a "producer" 401c, and the like.

The "reagent ID" 401a is a field in which the ID for identifying the reagent is displayed, the "reagent name" 401b is a field in which the name of the reagent is displayed, and the "producer" 401c is a field in which the producer of the reagent is displayed.

The reagent information display section 402 displays information of the reagent (reagent name: ccc in FIG. 5) selected in the reagent list display section 401. The selection of the reagent in the reagent list display section 401 is carried out by the operation of the user for specifying the reagent desired to select in the list. The selected reagent is highlight (emphasize) displayed in the reagent list display section 401.

The reagent information display section 402 also displays more detailed information associated with the selected reagent in addition to the information 402a, 402b, 402c corresponding to the information 401a, 401b, 401c displayed in the reagent list display section 401.

In the present embodiment, the detailed information of the reagent obtained by reading the barcode of the reagent container with the barcode reading unit 115 is automatically reflected on the information of the reagent displayed in the reagent list display section 401 and the reagent information display section 402, as well as, a measurement parameter setting screen 500, to be described later, but may be manually input by the user.

The operation display section 403 includes a "delete" button 403a, a "register button" 403b, and a "close" button 403c.

The "delete" button 403a is provided to delete the reagent selected in the reagent list display section 401.

The "register" button 403b is provided to register (save) the reagent information (includes measurement parameter) in the current setting content.

The "close" button 403c is provided to close the reagent master setting screen 400.

The reagent information display section 402 includes a "set measurement parameter" button 402d for setting the measurement parameter to be set in association with the relevant reagent.

When the "set measurement parameter" button 402d is selected, the measurement parameter setting screen 500 shown in FIG. 6 is displayed.

In the measurement parameter setting screen 500, a reagent ID 501 and a reagent name 502 of the reagent to which the measurement parameter is applied is displayed, and also a measurement item 503 in which the relevant reagent is used is displayed.

The measurement parameter setting screen 500 includes input boxes 504a to 504h for inputting set values of the plurality of measurement parameters. The values of the dispensing amount, the reaction time, and the like of the reagent are input to the input boxes 504a to 504h as set values of the measurement parameter. For example, when the measurement item is P-FDP (Fibrin/Fibrinogen Degradation Products), set values of sample aspiration amount, diluted solution amount, first reagent amount, warming time, second reagent amount, absorbance changing amount calculation start time, absorbance changing amount calculation end time, wavelength, and the like are input to the input boxes.

The processing for accepting the registration of the measurement parameter is carried out in the set parameter setting screen 500 as described above. The set value of the changed measurement parameter is registered in the measurement parameter storage section 123a.

The measurement parameter registration process by the processing device 102 (management program 123b) will now be described based on FIG. 7.

Figure 7:
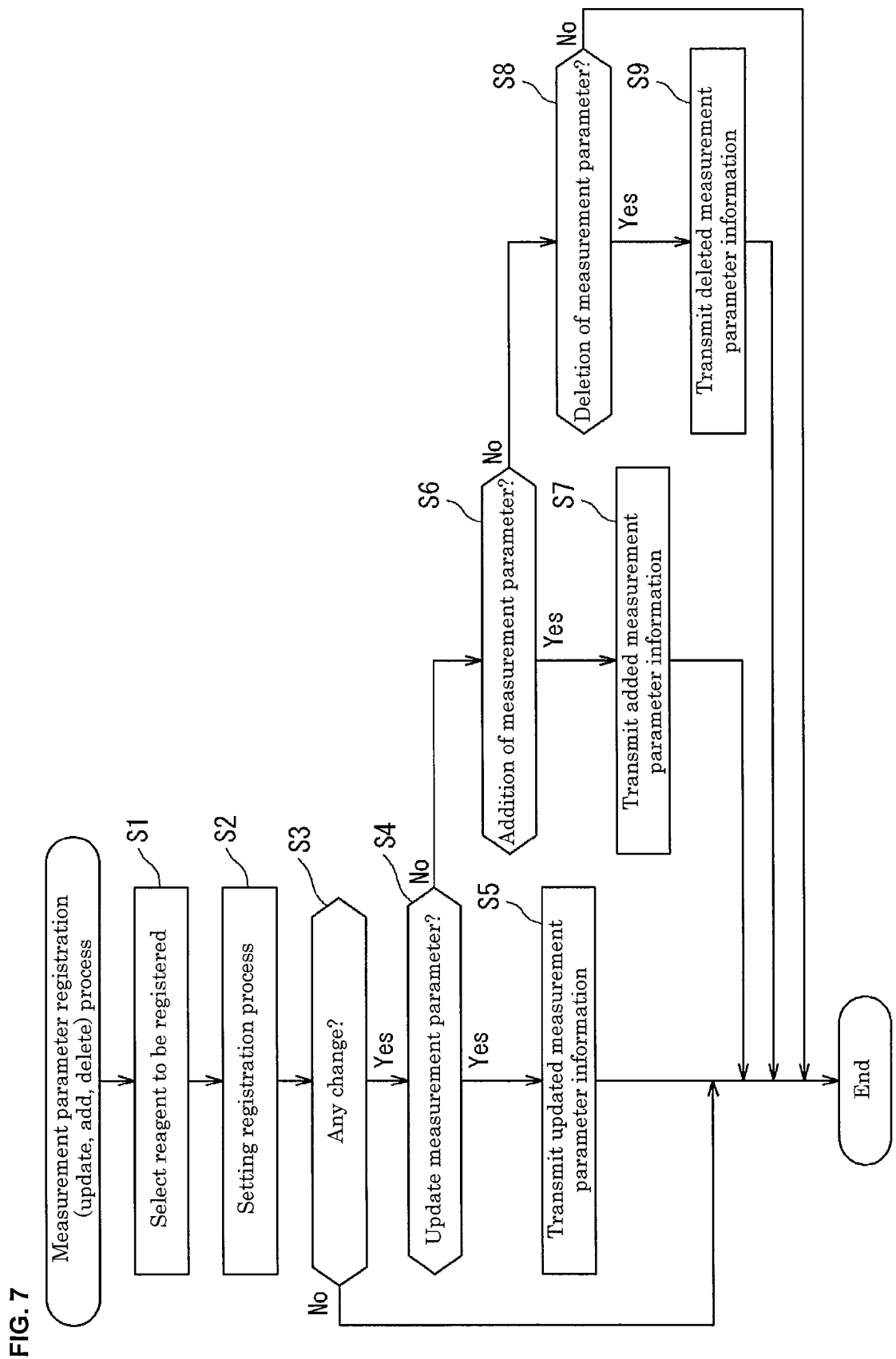
FIG. 7 shows one example of a flowchart of a measurement parameter registration process.

As shown in FIG. 7, when registering the measurement parameter in the analysis device 100, the processing for accepting the input operation for the selection (includes new registration) of the reagent to be registered is first carried out (step S1). The selection of the reagent is carried out by selecting the displayed reagent in the reagent master setting screen 400 shown in FIG. 5 (step S1).

Next, the set measurement parameter button 402 of the reagent master setting screen 400 is selected, whereby the measurement parameter setting screen 500 of FIG. 6 is displayed. In such parameter setting screen 500, the update/new registration (addition) of various types of set values to become the measurement parameter are carried out (step S2).

The registration type is "update" if the set value is changed to a new set value with the set value of the measurement parameter already set, and the registration types is "add" if the set value is newly set with the set value of the measurement parameter in the non-set state.

After the input of the set value in the measurement parameter setting screen 500 shown in FIG. 6 is terminated and the "register" button 403b of FIG. 5 is selected, the measurement parameter after the change (update/add) is registered in the measurement parameter storage section 123a.

When deleting the set measurement parameter, the "delete" button 403a is to be selected with the reagent to be desired to delete being selected in the reagent master setting screen 400 of FIG. 5. Thus, the measurement parameter corresponding to the reagent is deleted with the reagent information. When the measurement parameter is deleted, the registration type is "delete".

When the registration of the measurement parameter has been carried out in the screens 400, 500 of FIG. 5 and FIG. 6 (step S3), determination of the registration type is made (steps S4, S6, S8). When the registration type of the measurement parameter is "update" (step S4), the processing for transmitting to the management server 201 the transmission information including the updated measurement parameter from the wired communication section 126a or the wireless communication section 126b of the communication interface 126 is executed (step S5).

When the registration type of the measurement parameter is "add" (step S6), the processing for transmitting to the management server 201 the transmission information including the added measurement parameter from the wired communication section 126a or the wireless communication section 126b of the communication interface 126 is executed (step S7).

When the registration type of the measurement parameter is "delete" (step S8), the processing for transmitting to the management server 201 the transmission information including the deleted measurement parameter from the wired communication section 126a or the wireless communication section 126b of the communication interface 126 is executed (step S9).

Figure 8:
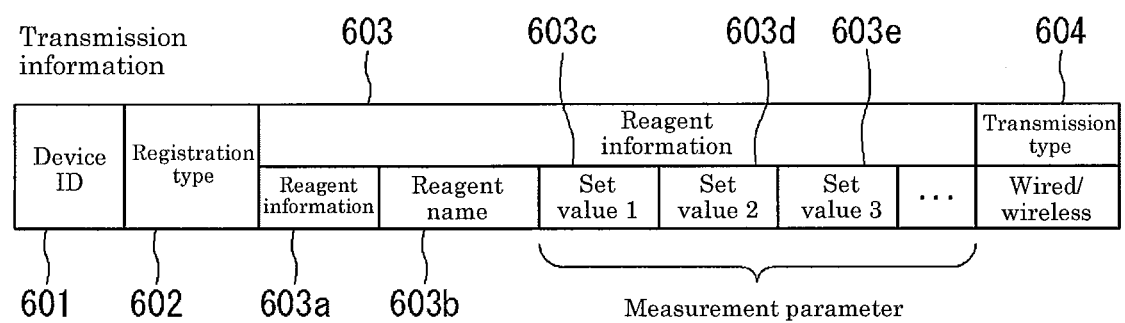
FIG. 8 is a schematic view showing one example of a data structure of transmission information.

The transmission information transmitted to the management server 201 has a data structure as shown in FIG. 8. That is, the transmission information includes a device ID 601, a registration type 602, reagent information 603, a transmission type 604, and the like.

The device ID 601 is the identification information indicating the analysis device 100 that has transmitted the transmission information.

The registration type 602 is the information (information indicating a transmission cause) indicating the registration type of the measurement parameter, and indicates one of update, add, and delete. The registration type 602 is also the information indicating that the measurement parameter has been changed.

The reagent information 603 includes a reagent name 603a, a measurement item name 603b, and a plurality of set values 603c, 603d, 603e. The reagent name 603a indicates the name of the reagent corresponding to the registered measurement parameter. The measurement item name 603b indicates the measurement item name measured by the reagent corresponding to the registered measurement parameter. The set values 603c, 603d, 603e indicate each set value of the registered measurement parameters.

The transmission type 604 is the information indicating whether the transmission of the transmission information from the analysis device 100 is carried out by the wired communication or is carried out by the wireless communication. If the transmission information is transmitted using the wired communication section (wired transmission section) 126a of the communication interface (transmission unit) 126 in the processing device 102 of the analysis device 100, the information indicating "wired" is stored in the transmission type 604. If the transmission information is transmitted using the wireless communication section (wireless transmission section) 126b, the information indicating "wireless" is stored in the transmission type 604.

The transmission information is also transmitted at a predetermined timing other than being transmitted with the registration of the measurement parameter as a trigger as in the previously described steps S5, S7, S9.

Figure 9:
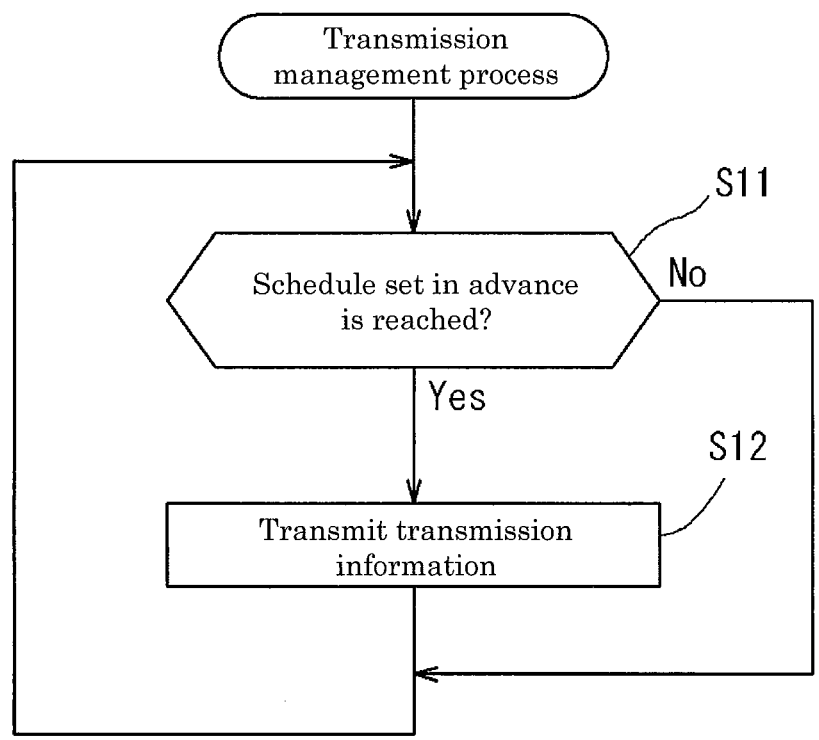
FIG. 9 shows one example of a flowchart of a transmission management process.

As shown in FIG. 9, the processing device 102 (management program 123b) constantly monitors whether or not a transmission schedule set in advance is reached (step S11), and transmits the transmission information (step S12) when the predetermined transmission schedule (timing) set in advance is reached.

The predetermined transmission schedule is set as a timing at which a lot of the reagent used in the analysis device 100 is switched, for example. The switching of the lot of the reagent can be detected by reading the barcode of the reagent container with the barcode reading unit 115 when the reagent of a new lot number is set in the reagent rack 114 with the replacement of the reagent.

When the lot of the reagent is switched, the transmission information including the reagent information (measurement parameter) on such reagent is generated, and transmitted from the processing device 102 to the management server 201. In such a case, the information indicating schedule transmission is set in the registration type 602 (information indicating transmission cause) of the transmission information rather than any one of update, add, or delete.

Since the transmission information is transmitted other than when the measurement parameter has been registered, the transmission frequency of the transmission information is increased and a great amount of information for management in the management server 201 is obtained.

The information (transmission information) associated with the reagent currently used in the analysis device 100 is transmitted other than when the measurement parameter has been registered such as at the time of switching of the lot of the reagent, and the like, so that the management server 201 can accurately grasp which reagent is currently being used.

The predetermined transmission schedule (timing) to transmit the transmission information may be the timing at which the reagent expired, and furthermore, may be an arbitrary date and time.

Figure 10:
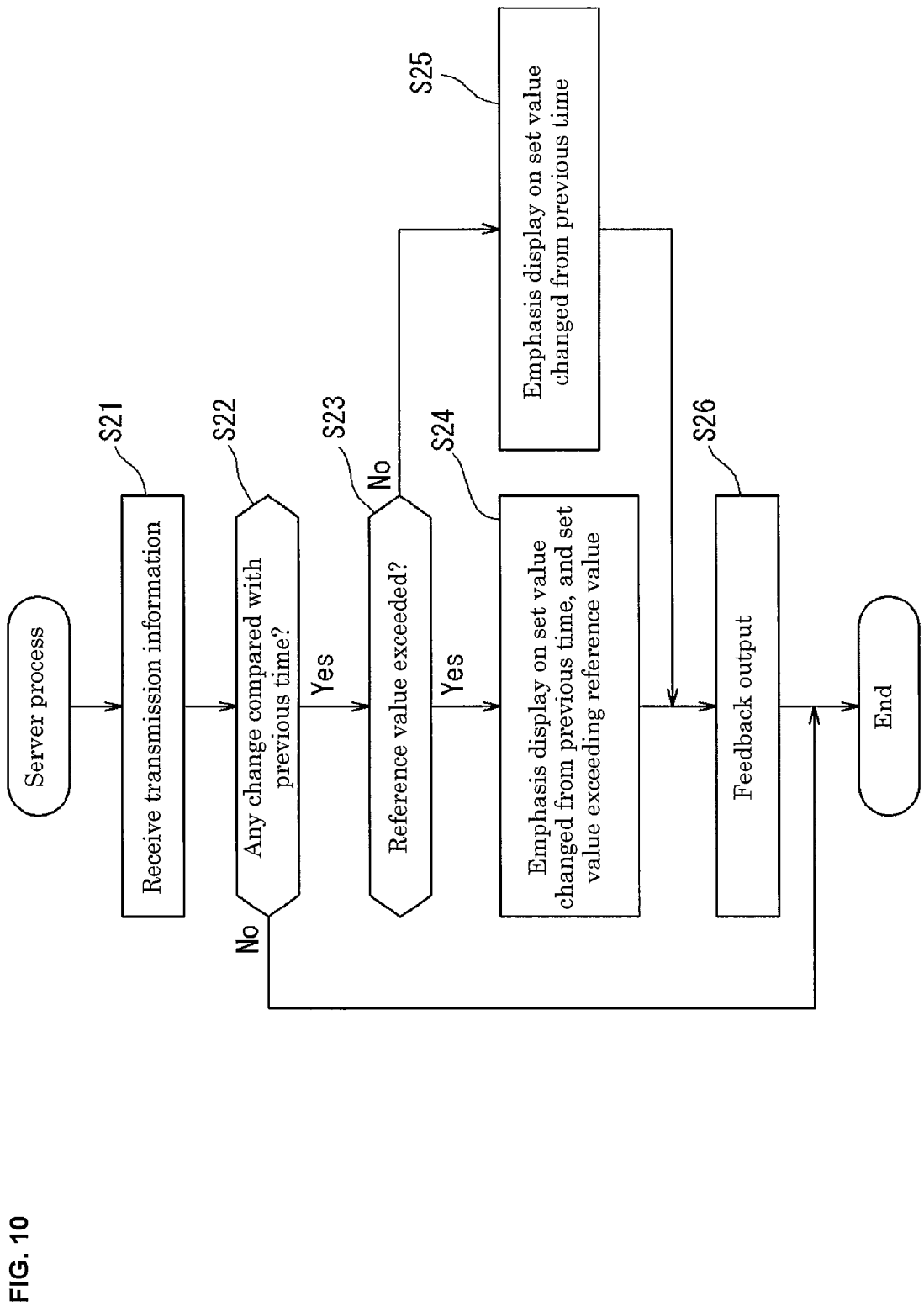
FIG. 10 shows one example of a flowchart of a server process.

The management server 201 (management program 223e) for receiving the transmission information carries out the server process shown in FIG. 10.

When receiving the transmission information from the analysis device 100 (receiving process; step S21), the management server 201 saves the transmission information in the transmission information storage section 223a. The measurement parameter included in the received transmission information is compared with the measurement parameter (transmission information) for the same reagent (measurement time) transmitted the previous time from the same analysis device 100, and whether or not the measurement parameter is changed is determined (step S22). The determination of step S22 may be made based on the registration type (information indicating the transmission cause) included in the received transmission information. That is, determination is made that there is change compared to the previous time if the registration type (information indicating the transmission cause) is update, add, or delete, and that there is no change in the measurement parameter if the registration type is the information indicating schedule transmission.

If there is change in the measurement parameter, the management server 201 assumes the received transmission information as the target of display. If there is no particular change, the management server 201 terminates the process without change. That is, if there is no change in the measurement parameter (such as in the case of schedule transmission, etc.), the information is not the target of display at the management server 201 or the terminal 202.

If there is change in the measurement parameter, the management server 201 determines whether the set value of the measurement parameter included in the received transmission information is within a range of the reference value registered in the reference value database 223b, or is beyond the range of the reference value (step S23).

After the determination of step S23 or in accordance with the operation by the personnel in the support center D, a measurement parameter registration check screen 700 shown in FIG. 11 is displayed on the display of the management server 201 or the terminal 202. In the measurement parameter registration check screen 700, the display information associated with the reagent such as a reagent ID 701, a reagent name 702, a measurement item 703, and the like is displayed based on the received transmission information, and in addition, set values 704a to 704h of the measurement parameter related to the registration are displayed (output process by the screen display; steps S24, S25). For example, when the measurement item is P-FDP, the set values of sample aspiration amount, diluted solution amount, first reagent amount, warming time, second reagent amount, absorbance changing amount calculation start time, absorbance changing amount calculation end time, wavelength, and the like are displayed.

The registration type (update, add, delete) of the measurement parameter may be displayed based on the received transmission information in the measurement parameter registration check screen 700.

The personnel of the support center D can grasp that the measurement parameter has been registered in the analysis device 100 by viewing the screen 700. As a result, if inappropriate measurement data is obtained using the analysis device 100, whether or not the registration of the measurement protocol by the user is performed is also grasped, and hence whether or not the cause of inappropriateness is the registration of the measurement protocol can be verified. Accordingly, the measurement data of the analysis device 100 can be more accurately managed.

After the determination of step S23 or in accordance with the operation by the personnel in the support center D, the measurement parameter registration check screen 700 shown in FIG. 11 is displayed on the display of the management server 201 or the terminal 202, but the present invention is not limited thereto. After the determination of step S23, the management server 201 may transmit to the portable telephone of the personnel who performs the maintenance, and the like of the analysis device, the measurement protocol of which device in which facility has been registered by e-mail. The management server 201 may include a speaker, so that after the determination of step S23, the management server 201 may report to the personnel the measurement protocol of which device in which facility has been registered by audio from the speaker in the support center D. Thus, the registration of the measurement protocol is automatically output rather than according to the operation by the personnel in the support center D, so that the registration of the measurement protocol can be reported to the personnel of the support center D in a more timely and reliable manner.

The display information associated with the reagent such as the reagent ID 701, and the like is generated by referencing the reagent database 233c based on the reagent name 603a included in the transmission information. The processing for referencing the reagent database 233c also serves as a processing for determining whether or not the reagent indicated by the reagent name 603a included in the transmission information is a predetermined reagent set in the management server 201 (management device 200).

If the reagent indicated by the reagent name 603a included in the transmission information is the reagent (unknown reagent) that is not registered in the reagent database 233c, the information indicating that the measurement parameter has been set (registered) for the unknown reagent is displayed in the screen 700 in place of the display information associated with the reagent.

Thus, the personnel of the support center D can recognize the start of usage of the unknown reagent. In the case of the unknown reagent, the reference (reference value) for determining whether or not the registration of the measurement parameter is appropriate is poor, and hence attention is particularly needed for the appropriateness in the registration of the measurement parameter.

Furthermore, in the measurement parameter registration check screen 700, the reference value 705 corresponding to a plurality of set values 704a, 704b, and 704c is displayed based on the reference value database 223b. The reference value 705 may not be displayed for the measurement parameter in which the reference value is not set in the reference value database 232b.

As shown in FIG. 11, in the measurement parameter registration check screen 700, the set values of the changed measurement parameter ("sample aspiration amount" 704a, "diluted solution amount" 704b, "first reagent amount" 704c of FIG. 11) are emphasis displayed, and the set values of the measurement parameter ("sample aspiration amount" 704a, "first reagent amount" 704c of FIG. 11) in which the set values of the measurement parameter included in the received transmission information are beyond the range of the reference value are emphasis displayed (step S24). The set value ("diluted solution amount" 704b of FIG. 11) that simply has change and the set value ("sample aspiration amount" 704a, "first reagent amount" 704c of FIG. 11) beyond the range of the reference value are emphasis displayed in a distinguishable manner (e.g., with different colors).

If all the set values of the changed measurement parameter are within the reference value, the emphasis display is made on the changed set values (step S25).

Thus, the personnel on the support center D side can easily determine if the registration of the measurement parameter is important or minor by determining whether or not the measurement parameter after the change exceeds the reference value in relation to the change in the measurement parameter, and then displaying the measurement parameter that exceeds the reference value and the measurement parameter that does not exceed the reference in a distinguished manner.

The registration of the measurement parameter in the range not exceeding the reference value may be assumed as a registration without any problem, and notification of registration may not be displayed even if the transmission information is received.

The determination on whether or not the registered measurement parameter exceeds the reference value is carried out on the analysis device 100 side, and the transmission information may be transmitted only for the registration of the measurement parameter exceeding the reference value. When making the determination based on the reference value on the analysis device 100 side, the reference value may be input/set on the analysis device 100 side or may be acquired by the analysis device 100 from the reference value database 223b of the management server 201.

FIG. 12 shows a measurement parameter reference value setting screen 800 for setting the reference value of the measurement parameter at the management server 201 or the terminal 202. The reference value of the measurement parameter can be set for every reagent (measurement item).

Other than being input with a reagent ID 801, a reagent name 802, and a measurement item 803 of a reagent to become a target for setting the reference value of the measurement parameter, the measurement parameter reference value setting screen 800 can be input with a range (upper limit and lower limit) of the reference value for a plurality of set values 804a to 804 configuring the measurement parameter. For example, when the measurement item is P-FDP, the range (upper limit and lower limit) of the reference value for the set values of sample aspiration amount, diluted solution amount, first reagent amount, warming time, second reagent amount, absorbance changing amount calculation start time, absorbance changing amount calculation end time, wavelength, and the like can be input. The reference value set in the measurement parameter reference value setting screen 800 is registered in the reference value database 232b.

In the present embodiment, the configuration in which the reference value has a range (upper limit and lower limit) for the plurality of reference values 804a to 804h corresponding to the measurement parameter in the measurement parameter reference value setting screen 800 for setting the reference value of the measurement parameter has been described, but the present invention is not limited thereto. The present invention may be such that the reference value does not have a range and the reference value may be one reference value set in advance, for example.

In step S24 or in both step S24 and step S25, the contact information (e.g., telephone number or e-mail address) of the inspection facility, in which the analysis device 100 registered with the measurement parameter is set, is displayed on the display of the management server 201 or the terminal 202 of the support center D. The contact information is displayed based on the user database 223d.

Thus, for example, when the measurement parameter of the analysis device 100c of the inspection facility C is registered (and when the measurement parameter exceeds the reference value), the personnel of the support center D may make a call to the inspection facility C, send an e-mail, or visit the inspection facility C to call the attention of the inspection facility C on the appropriateness of the registration of the measurement parameter.

The management server 201 determines whether or not the analysis device 100 that is a source of the transmission transmits with the wireless communication section (wireless transmission section) 126b based on the transmission type 604 of the received transmission information. That is, if the transmission type 604 of the received transmission information indicates "wireless", it is apparent that the analysis device 100 that is a source of the transmission transmits the transmission information with the wireless communication section 126.

If the transmission type 604 of the received transmission information indicates "wireless", the management server 201 performs a feedback output of reporting that the measurement parameter has been registered with respect to the analysis device 100 (step S26).

In the case of the analysis device that carries out communication with the management server 201 through the wireless communication as in the analysis device 100a of the facility A shown in FIG. 1, there is a possibility that the analysis device 100a will be moved to various places in the inspection facility or outside the inspection facility. Thus, even if the support center D attempts to contact the contact information grasped based on the user database 223d to call the attention involved in the registration of the measurement parameter, there is a possibility that the contact cannot be made.

Thus, with respect to the analysis device 100a that carries out the communication with the management server 201 through the wireless communication, the feedback output is carried out with respect to the analysis device 100a to directly call the attention to the user of the analysis device 100a. The content displayed on the processing device 102 of the analysis device 100a with the feedback output may be similar to or simpler than the screen 700 of FIG. 11.

The feedback output is preferably carried out only when the measurement parameter exceeds the reference value, but may be reported even when the reference value is not exceeded.

Furthermore, the feedback output may be carried out regardless of the transmission method (wireless/wired) of the analysis device 100.

The present invention is not limited to the embodiment described above, and various modifications may be made.

What is claimed is:
1. An analysis system comprising:
an analysis device that analyzes a sample using a reagent and that performs the analysis of the sample in accordance with a measurement parameter measured in relation to a reagent to be used; and
a management device communicably connected to the analysis device via a network; wherein the analysis device includes a first control unit that enables execution of processing for accepting a registration of the measurement parameter, and when the measurement parameter is registered, executes processing for transmitting to the management device transmission information including information indicating that the measurement parameter is registered;
the management device includes a display unit and a second control unit that executes a receiving process of receiving the transmission information transmitted from the analysis device and an output process of outputting information indicating that the measurement parameter is registered in the analysis device based on the received transmission information, wherein:
the second control unit enables execution of processing which determines whether or not the registered measurement parameter exceeds a range of a predetermined reference value and for controlling the display unit to display the registered measurement parameter that exceeds the reference value and the registered measurement parameter that does not exceed the reference in a distinguished manner.

2. The analysis system according to claim 1, wherein the transmission information includes information indicating a set value of a measurement parameter to be registered.

3. The analysis system according to claim 1, wherein the transmission information includes information indicating a registration type of the measurement parameter.

4. The analysis system according to claim 1, wherein the first control unit executes the processing for transmitting the set measurement parameter to the management device at a predetermined timing.

5. The analysis system according to claim 4, wherein the predetermined timing is a timing at which a lot of a reagent is switched.

6. The analysis system according to claim 1, wherein the transmission information includes identification information of the analysis device.

7. The analysis system according to claim 1, wherein the output process includes a process for feedback output of transmitting to the analysis device information for causing the analysis device to output the information indicating that the measurement parameter is registered in the analysis device with respect.

8. The analysis system according to claim 7, wherein
the analysis device includes a wireless transmission section that wirelessly transmits the transmission information;
the second control unit enables execution of processing for determining whether or not the transmission information is transmitted from the wireless transmission section; and
the feedback output is carried out when determined that the transmission information is transmitted from the wireless transmission section.

9. The analysis system according to claim 1, wherein the second control unit enables execution of processing for determining whether or not the set value of the registered measurement parameter is within a range of a predetermined reference value.

10. The analysis system according to claim 1, wherein the transmission information includes reagent information indicating a reagent corresponding to the measurement parameter; and
the second control unit enables execution of processing for determining whether or not a reagent indicated by the reagent information is a predetermined reagent set in the management device.

11. The analysis system according to claim 1, wherein the analysis device includes a storage unit that stores the measurement parameter; and
the first control unit enables execution of processing for accepting the registration of the measurement parameter stored in the storage unit.

12. The analysis system according to claim 1, wherein
the output process includes a process of causing the display unit to display the information that the measurement parameter is registered.

13. An analysis device that analyses a sample using a reagent and that performs the analysis of the sample in accordance with measurement parameter set in relation to a reagent to be used, the analysis device being communicably connected to a management device via a network; the analysis device comprising:
a first control unit that enables execution of processing for accepting registration of the measurement parameter, and when the measurement parameter is registered, executes processing for transmitting to the management device transmission information including information indicating that the measurement parameter is registered, wherein the transmission information includes information indicating a set value of a measurement parameter to be registered and the registered measurement parameter that exceeds the reference value and the registered measurement parameter that does not exceed the reference are displayed in a remote management device display in a distinguished manner.

14. The analysis device according to claim 13, wherein the transmission information includes information indicating a registration type of the measurement parameter.

15. The analysis device according to claim 13, wherein the control unit executes the processing for transmitting the set measurement parameter to the management device at a predetermined timing.

16. The analysis device according to claim 15, wherein the predetermined timing is a timing at which a lot of a reagent is switched.

17. A management device communicably connected via a network to an analysis device that analyses a sample using a reagent and that performs the analysis of the sample in accordance with measurement parameter set in relation to a reagent to be used, the management device comprising:
a display unit; and
a control unit that executes a receiving process of receiving transmission information including information indicating that the measurement parameter is registered in the analysis device from the analysis device, and an output process of outputting the information indicating that the measurement parameter is registered in the analysis device based on the received transmission information, wherein
the control unit enables execution of processing which determines whether or not the registered measurement parameter exceeds a range of a predetermined reference value and for controlling the display unit to display the registered measurement parameter that exceeds the reference value and the registered measurement parameter that does not exceed the reference in a distinguished manner.

18. The management device according to claim 17, wherein the transmission information includes information indicating a set value of a measurement parameter to be registered.

19. The management device according to claim 18, wherein the transmission information includes information indicating a registration type of the measurement parameter.

* * * * *